United States Patent [19]

Lindner et al.

[11] 4,292,141
[45] Sep. 29, 1981

[54] ISOLATION OF BUTADIENE FROM A C4-HYDROCARBON MIXTURE

[75] Inventors: Alfred Lindner, Bobenheim-Roxheim; Klaus Volkamer, Frankenthal; Ulrich Wagner, Limburgerhof; Dieter Pommer, Weisenheim; Klaus-Juergen Schneider, Neustadt; Harald Schwentker, Weisenheim, all of Fed. Rep. of Germany

[73] Assignee: BASF Aktiengesellschaft, Fed. Rep. of Germany

[21] Appl. No.: 68,741

[22] Filed: Aug. 22, 1979

[30] Foreign Application Priority Data

Sep. 15, 1978 [DE] Fed. Rep. of Germany ....... 2840124

[51] Int. Cl.³ .......................... B01D 3/40; C07C 7/08
[52] U.S. Cl. ........................................ 203/49; 203/52; 203/54; 203/58; 203/60; 203/62; 203/70; 203/71; 203/81; 203/82; 203/84; 585/810; 585/836; 585/865; 585/867
[58] Field of Search ...................... 203/51, 58, 56, 60, 203/70, 81, 84, 71, 74, 75, DIG. 19, 99, 52, 62, 54, 68, 82, 49; 585/833, 865, 810, 867, 802, 836

[56] References Cited

U.S. PATENT DOCUMENTS

| | | | |
|---|---|---|---|
| 3,114,783 | 12/1963 | Butler et al. | 203/60 |
| 3,280,085 | 10/1966 | Kleiss | 585/956 |
| 3,284,339 | 11/1966 | Begley et al. | 585/810 |
| 4,038,156 | 7/1977 | Knott et al. | 203/75 |
| 4,090,923 | 5/1978 | Haskell et al. | 203/51 |
| 4,128,457 | 12/1978 | Barba et al. | 203/74 |
| 4,141,925 | 2/1979 | Pavlov et al. | 203/60 |

*Primary Examiner*—Wilbur L. Bascomb, Jr.
*Attorney, Agent, or Firm*—Keil & Witherspoon

[57] ABSTRACT

A process for isolating butadiene, with the aid of a selective solvent, from a C4-hydrocarbon mixture which contains butadiene and small amounts of styrene and may contain oxygen, hydrocarbons more soluble than butadiene in the selective solvent and hydrocarbons less soluble than butadiene in the selective solvent, in which process the C4-hydrocarbon mixture is separated by extractive distillation into a distillate which contains the less soluble hydrocarbons, a stream of butadiene and a stream containing the more soluble hydrocarbons, and in which a mixture of styrene and C4-hydrocarbons is removed from the C4-hydrocarbon mixture in a distillation zone upstream of the extractive distillation, the top product of the said distillation zone being fed to the extractive distillation.

6 Claims, 3 Drawing Figures

ISOLATION OF BUTADIENE FROM A $C_4$-HYDROCARBON MIXTURE

The present invention relates to a process for isolating butadiene from a $C_4$-hydrocarbon mixture containing butadiene and small amounts of styrene.

The isolation of butadiene from butadiene-containing $C_4$-hydrocarbon mixtures by extractive distillation, using a selective solvent, has been disclosed. The butadiene obtained from the extractive distillation is in general subjected to an additional, conventional distillation.

An important use of the butadiene obtained by extractive distillation is the preparation of butadiene-styrene copolymers, wherein, after polymerization, a styrene-containing stream of waste butadiene is obtained. This waste stream can, for example, be burnt, but is advantageously recycled to a butadiene extraction unit. The styrene-containing stream of waste butadiene may in addition contain small amounts of oxygen, due to initiation of the polymerization by oxygen.

Direct recycling of the stream of waste butadiene, which contains small amounts of styrene and may contain oxygen, to a butadiene extraction unit would lead to undesirable polymer formation within the said unit, thereby substantially reducing the time for which the unit can be run before requiring shut-down.

It is an object of the present invention to provide a process for isolating butadiene, with the aid of a selective solvent, from a $C_4$-hydrocarbon mixture which contains butadiene and small amounts of styrene and may contain oxygen, by which process butadiene can be isolated from the $C_4$-hydrocarbon mixture without styrene entering the butadiene unit, so that the process can be carried out continuously for long periods.

We have found that this and other objects are achieved, according to the invention, by a process for isolating butadiene, with the aid of a selective solvent, from a $C_4$-hydrocarbon mixture which contains butadiene and small amounts of styrene and may contain oxygen, hydrocarbons more soluble than butadiene in the selective solvent, and hydrocarbons less soluble than butadiene in the selective solvent, in which process the $C_4$-hydrocarbon mixture is separated by extractive distillation into a distillate which contains the less soluble hydrocarbons, a stream of butadiene, and a stream containing the more soluble hydrocarbons, and in which a mixture of styrene and $C_4$-hydrocarbons is removed from the $C_4$-hydrocarbon mixture in a distillation zone upstream of the extractive distillation, the top product from the said distillation zone being fed to the extractive distillation.

In a preferred embodiment of the process, a second stream of liquid or gaseous hydrocarbons is at the same time fed to the upstream distillation zone. In this way, the loss of butadiene associated with the removal of the mixture of styrene and $C_4$-hydrocarbons can be kept particularly low.

The $C_4$-hydrocarbon mixtures containing small amounts of styrene are obtained, for example, in the preparation of butadiene-styrene copolymers. In addition to butadiene and styrene, such mixtures can contain cis-but-2-ene, trans-but-2-ene, 1,2-butadiene, butane, iso-butane, but-1-ene, but-1-yne, butenyne and $C_3$-hydrocarbons, eg. propane, propene, propadiene and propyne. In general, the $C_4$-hydrocarbon starting mixtures contain from 0.05 to 10% by weight, preferably from 0.1 to 5% by weight, of styrene.

According to the invention, a mixture of styrene and $C_4$-hydrocarbons is removed, advantageously as a bottom product, from the $C_4$-hydrocarbon starting mixture, containing small amounts of styrene, in a distillation zone upstream of the extractive distillation, and the top product of the upstream distillation zone is fed to the extractive distillation. In general, the mixture of styrene and $C_4$-hydrocarbons which is so removed contains from 0.5 to 30% by weight, preferably from 1 to 20% by weight, especially from 2 to 15% by weight, of styrene, the upper limit of the styrene content in general being imposed by the limit of the bottom temperature. In order to minimize the tendency of styrene and butadiene to polymerize, the upstream distillation zone is advantageously operated with a very low bottom temperature which is in general from 40° to 70° C., preferably from 45° to 50° C.

On the other hand, it is advantageous to produce the reflux in the column by condensing the $C_4$-hydrocarbons with cooling water. This results in a high content of $C_4$-hydrocarbons in the bottom product, and hence a substantial loss of butadiene. In an advantageous embodiment of the process according to the invention, this loss of butadiene, associated with removal of the mixture of styrene and $C_4$-hydrocarbons, can be kept very low. The said advantageous embodiment comprises simultaneously feeding to the upstream distillation zone a second stream of liquid or gaseous hydrocarbons.

The liquid or gaseous hydrocarbons fed as a second stream to the distillation zone are in general $C_3$- and/or $C_4$-hydrocarbons. Advantageously, hydrocarbons having a lower butadiene content than the $C_4$-hydrocarbon starting mixture, for example containing less than 90% of the butadiene content of the $C_4$-hydrocarbon starting mixture, are employed, and preferably the hydrocarbons are substantially free from butadiene, for example contain less than 5% by weight, advantageously less than 1% by weight, of butadiene. Advantageously, saturated and/or monoolefinically unsaturated $C_3$- and/or $C_4$-hydrocarbons are used. Examples of suitable hydrocarbons are propane, propene, the butanes, n-butene, isobutene, the 2-butenes, 1,2-butadiene and mixtures containing these hydrocarbons. The use of $C_4$-hydrocarbon mixtures is particularly advantageous. In a preferred embodiment of the process, the raffinate, containing butanes and butenes, obtained from the extractive distillation is used.

In general, the second stream of hydrocarbon, to be fed to the upstream distillation zone, is introduced into the latter at or advantageously below the feed point of the $C_4$-hydrocarbon starting mixture containing small amounts of styrene, the preferred point of introduction being in the lower one-third, advantageously in the lower one-quarter, or especially in the bottom, of the upstream distillation zone. By introducing the second stream of hydrocarbon below the feed point of the $C_4$-hydrocarbon starting mixture, a counter-current scrubbing action results, giving, as the bottom product, a mixture of styrene and $C_4$-hydrocarbons of low butadiene content, for example less than 30% by weight, preferably less than 5% by weight, so that by using this procedure the loss of butadiene associated with the removal of the styrene can be kept particularly low. In a preferred embodiment of the process according to the invention, the second stream of hydrocarbon is admixed to the vapor, rising from the bottom, of the material from the upstream distillation zone, or is fed as a liquid to the bottom.

In addition to styrene, the C$_4$-hydrocarbon starting mixture used according to the invention may also contain small amounts of oxygen. In that case, the starting mixture is advantageously first fed to a distillation zone for removing oxygen, wherein an oxygen-containing top product and a styrene-containing bottom product are obtained. The latter is then used as the feed for the distillation zone upstream of the extractive distillation.

The distillation zone for the removal of oxygen can be provided with its own boiler in order to generate the vapor required for the separation. In a preferred embodiment of the process according to the invention, a part of the top product of the distillation zone upstream of the extractive distillation, in general from 5 to 50%, preferably from 10 to 20%, of this top product, is fed, preferably as a gaseous stream, to the bottom of the distillation zone for the removal of oxygen.

The two distillation zones can be arranged as separate constructions in two columns or as a combined construction in one column. The latter arrangement is preferred, and in that case the bottom of the distillation zone for the removal of oxygen can be constructed as a take-off tray. In this way, investment expense can be reduced, since the bottom pump and boiler of the distillation zone for the removal of oxygen can be dispensed with, and only one column is required for the two distillation zones.

The top product from the distillation zone upstream of the extractive distillation can be fed to the extractive distillation without mixing it with other butadiene-containing C$_4$-hydrocarbon mixtures. Advantageously, however, the top product is fed into a butadiene-containing C$_4$-hydrocarbon mixture, constituting the main feed stream of the extractive distillation, before being fed to the extractive distillation. Such butadiene-containing C$_4$-hydrocarbon mixtures to be used as the main feed stream for the extractive distillation are obtained, for example, as hydrocarbon fractions in the manufacture of ethylene and/or propylene by thermal cracking of a petroleum fraction, for example of liquified petroleum gas (LPG), naphtha, gas oil and the like. Further, such C$_4$-fractions are obtained by catalytic dehydrogenation of n-butane and/or n-butene.

Suitable selective solvents are carboxylic acid amides, such as dimethylformide, diethylformamide, dimethylacetamide, formylmorpholine, acetonitrile, furfurol, N-methylpyrrolidone, butyrolactone, acetone and mixtures of these with water. N-methylpyrrolidone is a particularly advantageous selective solvent.

Examples of hydrocarbons which are more soluble than butadiene in the selective solvent are vinylacetylene, ethylacetylene and 1,2-butadiene. Examples of hydrocarbons which are less soluble than butadiene in the selective solvent are the butanes, the n-butenes and isobutene.

The extractive distillation can be carried out using one extractive distillation zone. However, the process for isolating butadiene is particularly advantageously carried out by using two extractive distillation zones in series, with the same selective solvent. In that case, for example, a distillate (raffinate) containing the less soluble hydrocarbons, and an extract containing butadiene, the more soluble hydrocarbons, and the selective solvent, are obtained in the first stage of the extractive distillation. The extract is freed from the selective solvent, giving a mixture of butadiene and the more soluble hydrocarbons. This mixture is subjected to a second extractive distillation with the selective solvent in a second extractive distillation zone, giving butadiene as the distillate, and an extract which contains the more soluble hydrocarbons, including the higher acetylenes, any residual butadiene, and the selective solvent. The extract obtained is subsequently freed from the selective solvent, giving a hydrocarbon stream containing the more soluble hydrocarbons, including the C$_4$-acetylenes.

The butadiene obtained from the extractive distillation is in general subjected to a downstream distillation, for example in one or two distillation columns, in order to remove small amounts of propyne and C$_5$-hydrocarbons which may still be present. However, the removal of propyne and C$_5$-hydrocarbons by distillation can also be carried out upstream of the extractive distillation.

To avoid undesirable polymer formation it can be advantageous not only to remove styrene from the C$_4$-hydrocarbon starting mixture in the upstream distillation zone but also to add polymerization inhibitors in the conventional manner during the subsequent extractive distillation. Examples of suitable polymerization inhibitors are furfurol, benzaldehyde, aliphatic or aromatic nitro compounds, hydroquinone, sulfur, sodium nitrite, phenolic compounds, eg. 4-tert.-butyl-catechol, and aromatic amines, eg. napthylamine. In this way, the tendency of butadiene to polymerize can be reduced further. These inhibitors can equally be employed in the distillation zone in which the styrene is separated off.

Figure 1:
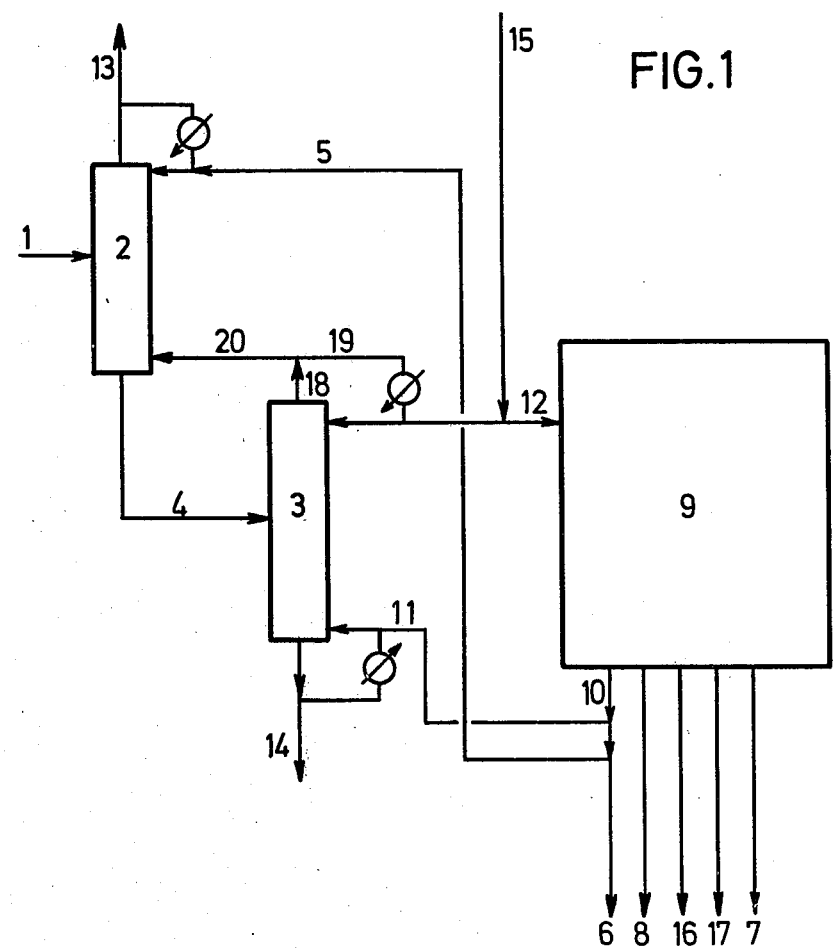
FIG. 1 is a flow diagram of one embodiment of the invention.

FIG. 1 shows an embodiment of the process according to the invention. A C$_4$-hydrocarbon mixture containing small amounts of oxygen and styrene is introduced through line 1 into the middle one-third of the distillation zone 2. At the top of the column 2, a part-stream of the raffinate from a downstream butadiene isolation unit 9 is introduced through line 5. Oxygen-free hydrocarbon mixture from the bottom of the distillation zone 2 is introduced through line 4 into the middle one-third of the distillation zone 3. At the top of the distillation zone 2, oxygen-containing C$_4$-hydrocarbon mixture 13 is taken off. At the bottom of the distillation zone 3, raffinate from a downstream butadiene isolation unit is fed in through line 11. Styrene-containing C$_4$-hydrocarbon mixture, having a low butadiene content, is taken off the bottom of the distillation zone 3 through line 14. At the top of the distillation zone 3, styrene-free and oxygen-free mixture is taken off (through lines 18 and 19) and is fed, with or without admixture of other C$_4$-hydrocarbon mixtures (from line 15), to the butadiene unit through line 12, in which unit it is separated by extractive distillation, using a selective solvent (N-methylpyrrolidone) into a fraction (raffinate) 10, containing the butenes, a stream of crude butadiene and the stream 8 containing the C$_4$-acetylenes. The stream of crude butadiene and the C$_3$- and C$_5$-hydrocarbons, and 1,2-butadiene, contained therein, are separated by distillation into the propyne stream 16, the 1,2-butadiene stream 17 and the pure butadiene stream 7. The part-stream of the raffinate which remains after taking off the streams 5 and 11 is taken off through line 6. A part of the top product of the distillation zone 3 is fed through lines 18 and 20 to the bottom of the distillation zone 2.

Figure 2:
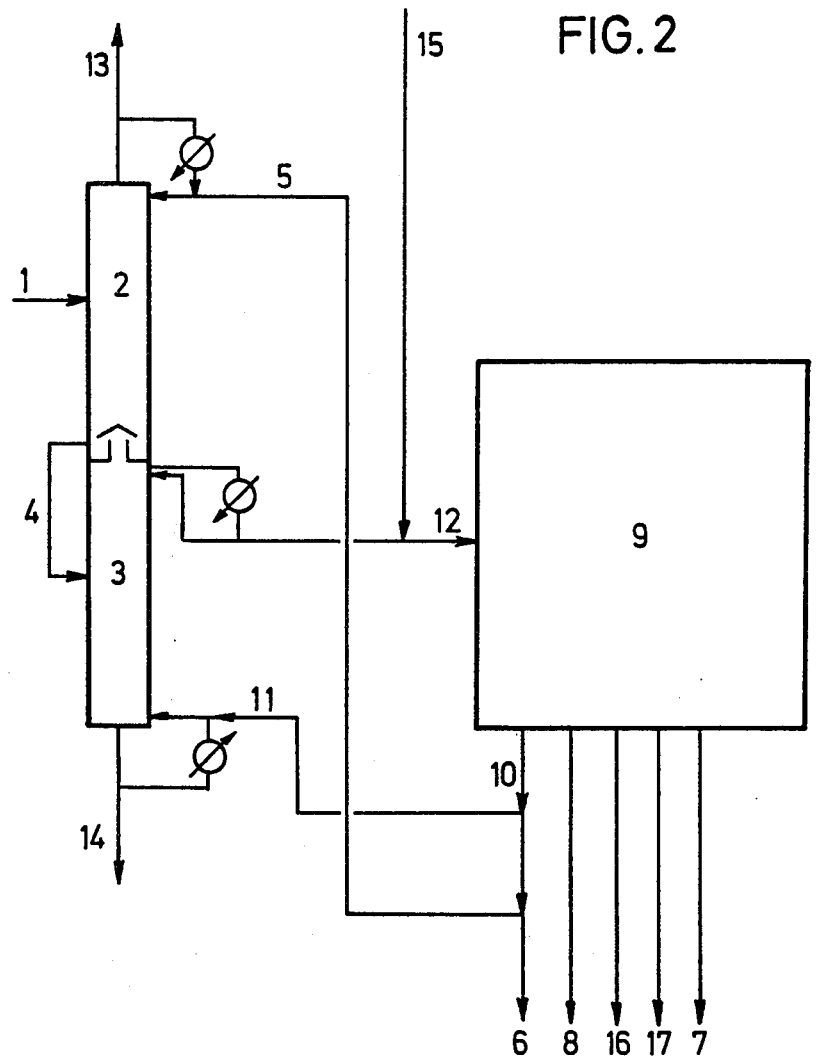
FIG. 2 is a flow diagram of a second embodiment of the invention.
Figure 3:
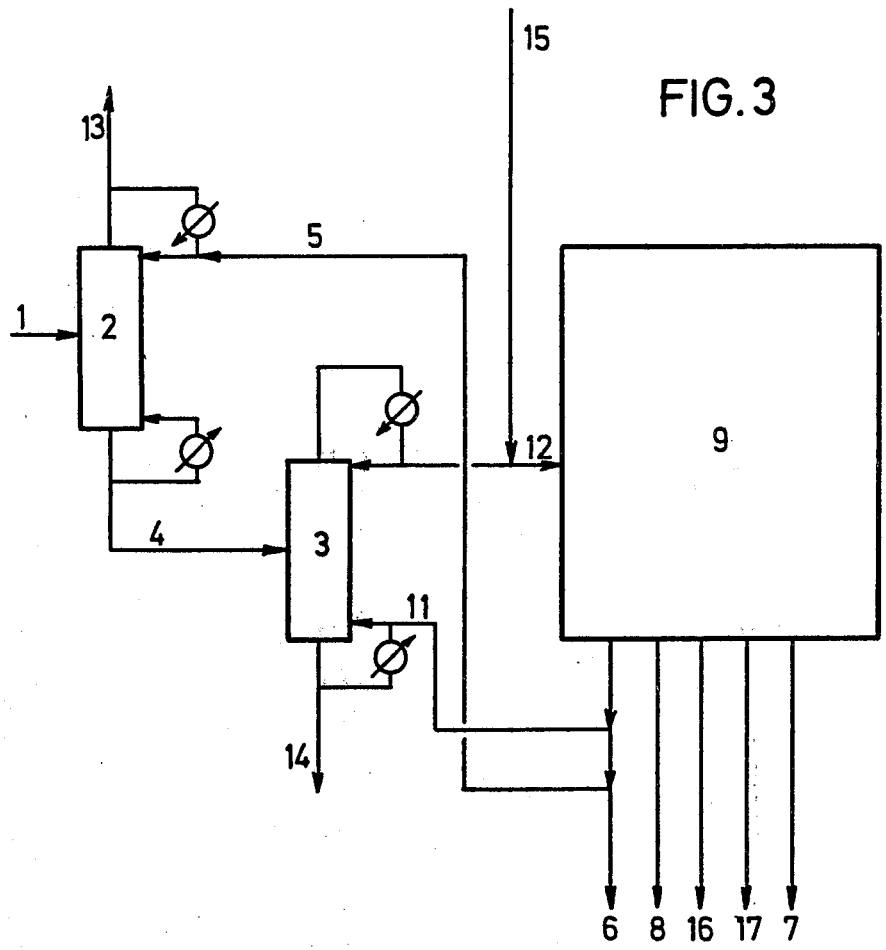
FIG. 3 is a flow diagram of a third embodiment of the invention.

Distillation zones 2 and 3 can be separate columns, as shown in FIG. 1, or can be a combined structure, in which case the bottom of the distillation zone 2 can be constructed as a take-off tray (FIG. 2). The process can however also be carried out as shown in FIG. 3, with two separate, conventionally connected columns, ie. without recycling top product from distillation zone 3 into distillation zone 2.

The Example which follows illustrates the invention.

EXAMPLE

A $C_4$-hydrocarbon mixture of the composition shown below is separated in an apparatus of the type shown in FIG. 2:

|  | % by weight |
|---|---|
| Isobutene | 2 |
| Trans-but-2-ene | 4 |
| Cis-but-2-ene | 15.67 |
| 1,3-butadiene | 75.0 |
| 1,2-butadiene | 0.2 |
| Butyne | 0.1 |
| Vinylcyclohexene | 2.0 |
| Styrene | 1.0 |
| Oxygen | 0.03 |

450 g/h of this hydrocarbon mixture are introduced, through line 1, on to the 4th tray, counting from the bottom, of the upper part 2, comprising 5 trays, of the column. At the top of the column, 1.6 g/h of a mixture of 12.9% by weight of oxygen and 87.1% by weight of hydrocarbons is removed through line 13. The pressure at the top is kept at 4.2 bar. The liquid bottom product is fed on to the 5th tray of the lower part 3, comprising 9 trays, of the column. At the bottom, the temperature is maintained at 42.7° C. by varying the amount taken off. By additionally introducing butenes (through line 5) at the top of the distillation column 2 used to remove oxygen, the loss of butadiene in the oxygen-containing top product from this distillation can be reduced.

At the top of the lower part 3 of the column, a part of the hydrocarbon vapor is allowed to enter the upper part from below. Another part is taken off (through line 12) as a styrene-free product containing 0.2 ppm (by weight) of oxygen. If 500 g/h of a butene mixture are introduced at the bottom of the lower part of the column (through line 11), a bottom product containing only 5% of butadiene is obtained.

The butene mixture employed has the following composition:

|  | % by weight |
|---|---|
| $C_3$-hydrocarbons | 0.7 |
| Butane | 13.6 |
| Iso-butane | 3.4 |
| But-1-ene | 26.5 |
| Iso-butene | 39.7 |
| Trans-but-2-ene | 8.6 |
| Cis-but-2-ene | 7.2 |
| 1,3-butadiene | 0.2 |
| $C_5$-hydrocarbons | 0.1 |

In this procedure, the loss of butadiene in the bottom product is 0.8%.

If only 150 g/h of the butene mixture are introduced, under otherwise identical conditions, the loss of butadiene in the bottom product increases to 4.7%. Without introducing the butene mixture, the loss of butadiene in the bottom product is 14.5%, based on the amount of butadiene in the feed product.

The styrene-free $C_4$-hydrocarbon mixture taken off through line 12 is mixed with a $C_4$-fraction, from an ethylene unit, supplied through line 12, and the $C_4$-hydrocarbon mixture obtained is separated by extractive distillation, using N-methylpyrrolidone as the selective solvent, in the extractive distillation unit 9.

We claim:

1. A process for isolating butadiene, with the aid of a selective solvent, from a $C_4$-hydrocarbon mixture which contains butadiene, small amounts of styrene, hydrocarbons more soluble than butadiene in the selective solvent and hydrocarbons less soluble than butadiene in the selective solvent, which process comprises:
   (a) subjecting the styrene-containing $C_4$-hydrocarbon mixture to distillation in a distillation zone upstream of an extractive distillation in a butadiene isolation plant,
   (b) feeding at the same time a second stream of liquid or gaseous $C_3$- and/or $C_4$-hydrocarbons to the upstream distillation zone at or below the point where the styrene-containing $C_4$-hydrocarbon mixture is fed to the upstream distillation zone,
   (c) removing a mixture of styrene and $C_4$-hydrocarbons from the $C_4$-hydrocarbon mixture as bottom product of the upstream distillation zone and obtaining as top product of the upstream distillation zone a styrene-free $C_4$-hydrocarbon mixture, and
   (d) subjecting the styrene-free $C_4$-hydrocarbon mixture to extractive distillation with the aid of the selective solvent in the downstream butadiene isolation plant,
   (e) wherein the styrene-free $C_4$-hydrocarbon mixture is separated into a distillate containing the hydrocarbons less soluble than butadiene, a stream containing butadiene and a stream containing the hydrocarbons more soluble than butadiene.

2. The process of claim 1, wherein the second stream fed to the upstream distillation zone is a saturated or monoolefinically unsaturated $C_4$-hydrocarbon or a mixture of saturated and/or monoolefinically unsaturated $C_4$-hydrocarbons.

3. The process of claim 1 or 2, wherein the second hydrocarbon stream is introduced into the lower one-third of the upstream distillation zone.

4. The process of claim 1 or 2, wherein oxygen is present in the styrene-containing $C_4$-hydrocarbon mixture and wherein the styrene-containing $C_4$-hydrocarbon mixture is first fed to a distillation zone for removing oxygen in which zone an oxygen-containing top product and a styrene-containing bottom product is used as the feed for the upstream distillation zone.

5. The process of claim 4, wherein a part of the top product from the upstream distillation zone is fed to the bottom of the distillation zone for the removal of oxygen.

6. The process of claim 1, wherein the top product from the distillation zone upstream of the extractive distillation is fed to a butadiene-containing $C_4$-hydrocarbon mixture, which constitutes the main feed stream for the extractive distillation, before being fed to the extractive distillation.

* * * * *